United States Patent [19]
Nixon et al.

[11] Patent Number: 5,473,784
[45] Date of Patent: Dec. 12, 1995

[54] BODY BOARD

[75] Inventors: Drue C. Nixon; Daniel B. Soulvie, both of Glendale; Richard T. Coughlin, Tempe, all of Ariz.

[73] Assignee: Arizona E.M.S. Products, Inc., Peoria, Ariz.

[21] Appl. No.: 277,189

[22] Filed: Jul. 19, 1994

[51] Int. Cl.$^6$ ................................................ A61G 1/00
[52] U.S. Cl. ................................................ 5/625; 5/601
[58] Field of Search .................. 5/625, 628, 601; 378/209, 210; 128/870

[56] References Cited

U.S. PATENT DOCUMENTS

| | | | |
|---|---|---|---|
| 3,840,221 | 10/1974 | Hogan | 5/625 |
| 4,226,231 | 10/1980 | Andersen | 128/870 |
| 4,369,982 | 1/1983 | Hein et al. | 5/625 |
| 4,584,729 | 4/1986 | Roberts et al. | 5/628 |
| 4,854,305 | 8/1989 | Bremer | 128/75 |
| 4,895,173 | 1/1990 | Brault et al. | 128/870 |
| 5,016,620 | 5/1991 | Matthews | 128/78 |
| 5,048,134 | 9/1991 | Dennill et al. | 5/82 R |
| 5,088,137 | 2/1992 | Rose | 5/625 |
| 5,113,876 | 5/1992 | Herman | 128/870 |
| 5,190,056 | 3/1993 | Hull | 128/870 |
| 5,263,213 | 11/1993 | Robertson et al. | 5/625 |
| 5,274,864 | 1/1994 | Morgan | 5/625 |

FOREIGN PATENT DOCUMENTS

| | | | |
|---|---|---|---|
| 123474 | 10/1984 | European Pat. Off. | 5/625 |
| 2271805 | 12/1975 | France | 5/625 |
| 2182570 | 5/1987 | United Kingdom | 5/625 |

*Primary Examiner*—Michael J. Milano
*Attorney, Agent, or Firm*—Fitch, Even, Tabin & Flannery

[57] ABSTRACT

A body board is provided having upper and lower plastic components defining an outer plastic shell having a hollow interior. The underside of the plastic shell defines a pair of runners which serve to space handholds disposed about the periphery of the body board from the ground on which the body board rests. A fiberglass reinforcement structure having upper and lower sheets is disposed within the hollow interior. The fiberglass sheets are bent or curved across the width of the body board to provide increased structural support for resistance to deflection or sagging of the body board when supporting a patient. The thickness of the upper and lower plastic shell components and the thickness of the upper and lower sheets of the fiberglass reinforcement structure are substantially uniform over a central x-ray region. Also, none of the upper and lower plastic shell components or the upper and lower fiberglass sheets extend vertically over any portion thereof disposed within the central x-ray region. Hence, x-rays passed through the x-ray region of the body board are absorbed by the body board substantially uniformly, without producing any lines of high density on x-ray film. The x-ray region may include the runners, and no lines of high density are realized at the runners despite the increased thickness at the runners. Identifying indicia may be formed in the underside of the outer plastic shell by a manner in which the indicia do not produce high density images on x-ray film.

8 Claims, 5 Drawing Sheets

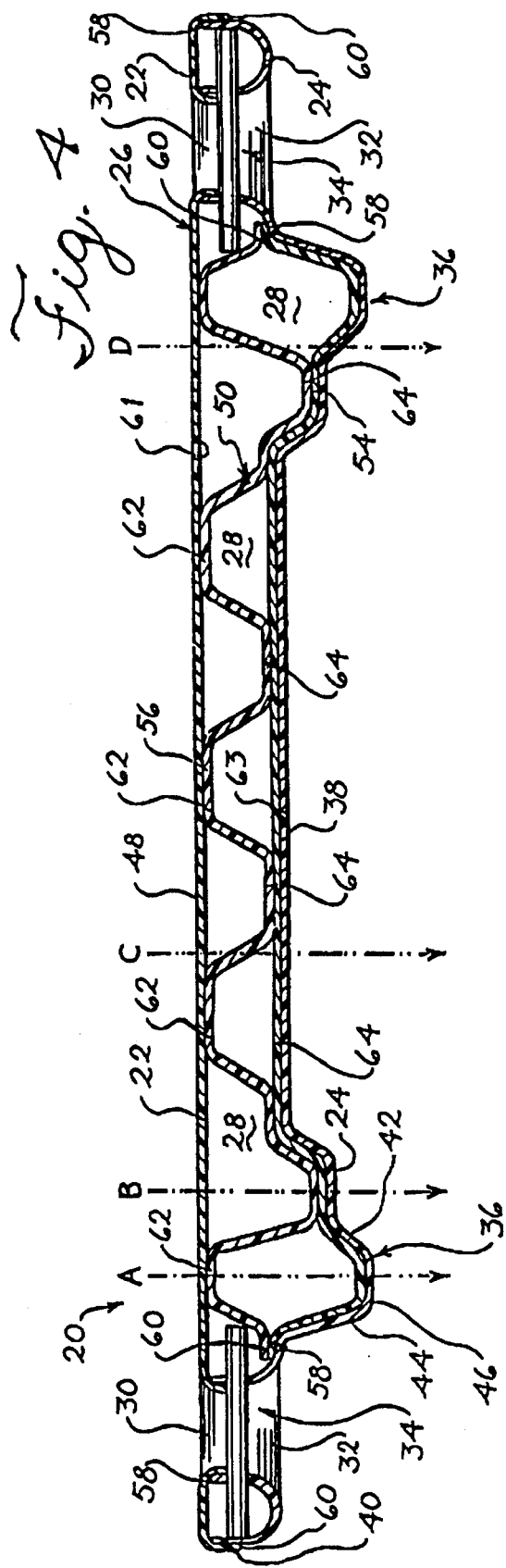

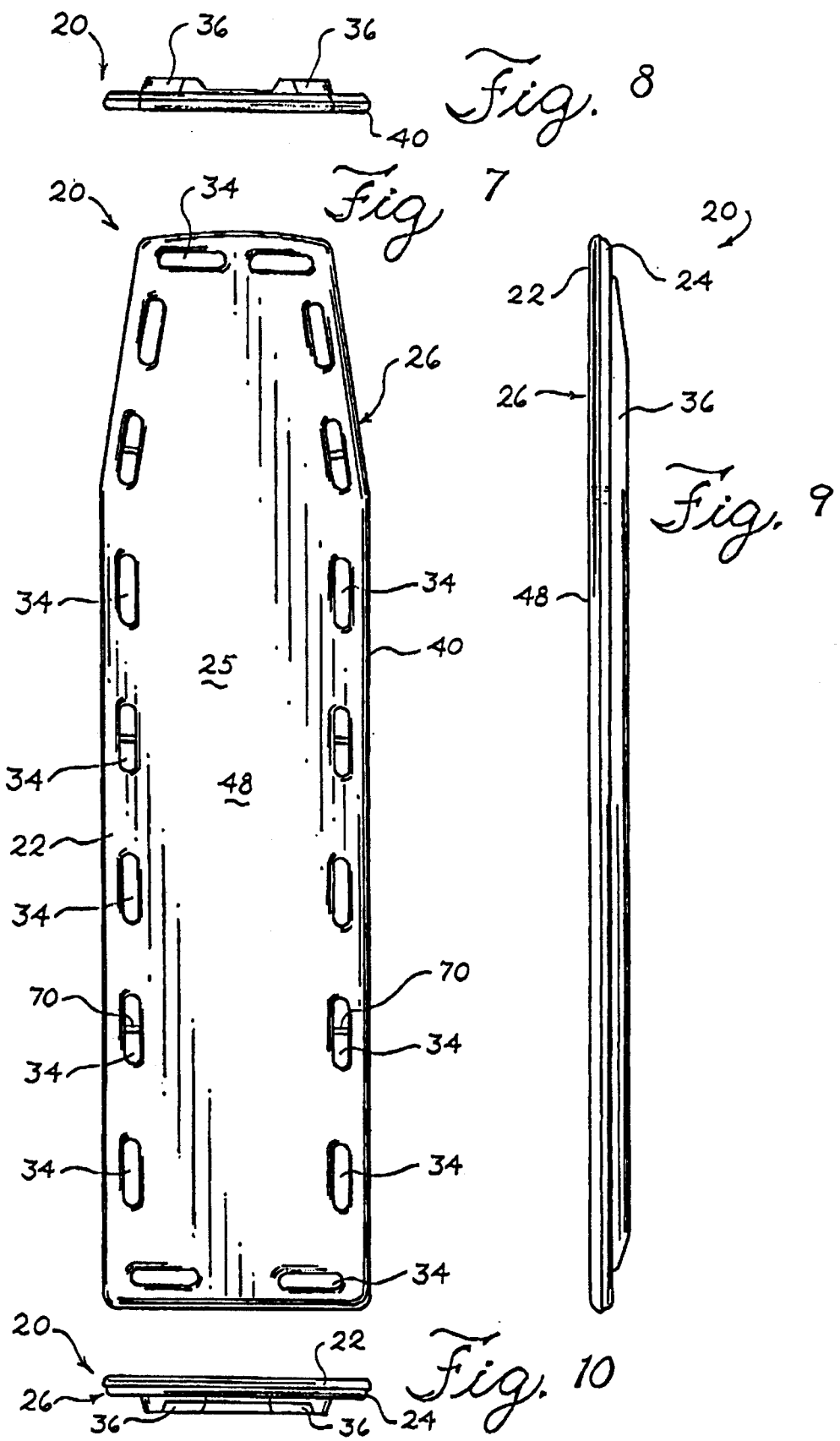

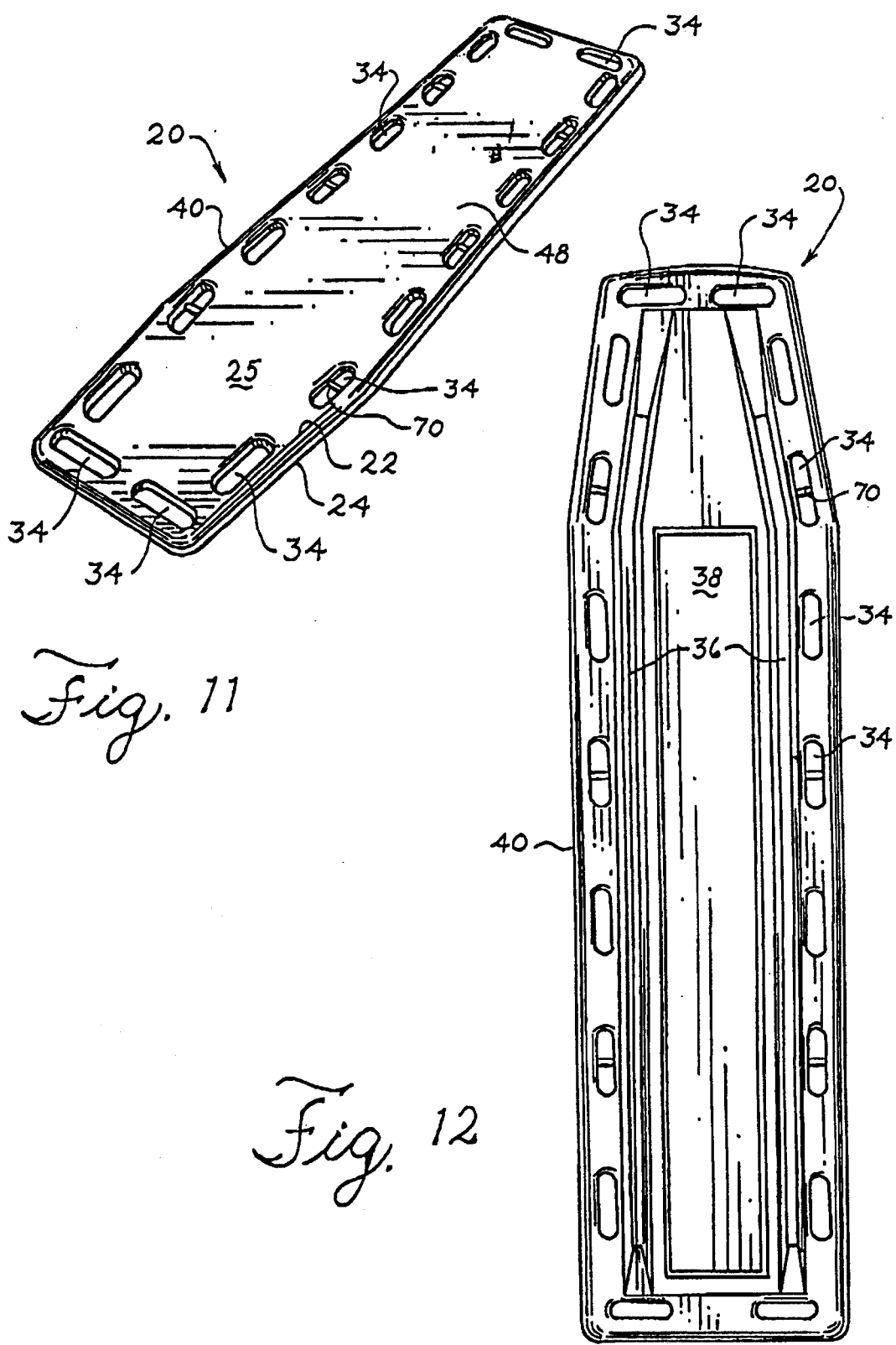

BODY BOARD

FIELD OF THE INVENTION

The present invention pertains to body boards for transporting injured persons, and more particularly, pertains to body boards suitable for use in radiography.

BACKGROUND OF THE INVENTION

Body boards for supporting injured persons during transport to a medical facility are currently in widespread use. Body boards typically consist of a flat, elongated piece of plywood upon which the injured person rests. The board has slots, which serve as handholds, disposed near its periphery, into which paramedics insert their hands to lift and carry the injured person upon the body board. Flat wooden body boards have been found to suffer numerous shortcomings. One shortcoming is that wood absorbs blood, and with recent concerns about transmission of AIDS, hepatitis, and the like through blood, wooden body boards are undesirable.

Accordingly, body boards have been molded of flat sheets of solid plastic. Such flat sheets of solid plastic have been found undesirable due to their heaviness. Thus, body boards have been made having a thin outer shell of hard plastic with the interior filled with polymeric foam. While this overcomes the heaviness problem of solid plastic boards, foam filled boards have been found to suffer from inadequate strength. The inadequate strength of foam filled body boards results in significant sagging or deflection of the board when subjected to the load of a fairly heavy person. Deflection of body boards is highly undesirable because in many instances, such as cervical or spinal injuries, it is important that the injured person be completely immobilized on a flat surface to avoid exacerbating the individual's injury and causing further trauma. Thus, there is a need for a body board having less weight than solid plastic body boards, while also having greater strength than foam filled body boards.

Another significant shortcoming of the aforementioned flat body boards currently in widespread use is that when the body board is laid on flat ground to slide an injured person onto the body board, the handholds are also positioned flat against the ground, whereby the user cannot insert their fingers completely through the handholds. Hence, the user is required to raise one side of the body board off the ground a sufficient amount that they can insert their fingers through the handholds and grip the board at the handholds. Since it is important that injured persons be supported on a level, flat surface, the requirement of tilting the board prior to lifting is extremely undesirable. There is a need for a body board which provides easy access to its handholds without having to first raise or tilt the body board.

In addition to overcoming each of the aforementioned shortcomings of currently existing body boards, the body board should be suitable for use in radiography, such as x-raying a patient while lying on the body board. In this regard, the body board should be constructed so as not to form lines of high density on x-ray film with x-rays taken through the body board.

SUMMARY OF THE INVENTION

In accordance with the present invention, a body board is provided having an outer plastic shell which prevents absorption of blood. Upper and lower elongated plastic components are bonded together about their peripheries to define a hollow interior region. The bonded upper and lower components also define a plurality of handholds about their periphery. The upper component defines a flat supporting surface for supporting an injured person. The lower plastic component defines a pair of runners on the underside of the body board which serve to space the handholds from the ground or other surface on which the body board rests. The provision of the runners on the underside of the body board thus provides easy access to the handholds for insertion of fingers through the handholds, without the requirement of first raising or tilting the body board.

The provision of the runners on the underside of the body board, while advantageous for elevating the handholds, produce a body board having non-uniform thickness. That is, the body board is thicker at the runners than it is over the portion of the body board between the runners. With conventional body boards formed of solid plastic and/or body boards formed of a thin plastic shell with a foamed polymeric filling, the relatively large thickness of the body board at the location of the runners would require that x-rays pass through a greater amount of material at the runners than over the thinner portions of the body board. This results in lines of high density on x-rays taken through the body board at the location of the runners. To provide substantial uniformity in x-ray absorption over a predetermined x-ray region, rather than filling the outer plastic shell with polymeric foam, a FIBERGLASS sheet reinforcement structure is disposed within the hollow interior of the outer plastic shell spanning the x-ray region. The sheets of FIBERGLASS are uniform in thickness across the width of the x-ray region and curved several times across the width of the spineboard to provide increased structural support. The FIBERGLASS sheets do not extend vertically over any portion. The upper and lower shell components are also uniform in thickness across the width of the x-ray region of the body board. Thereby, the combined thicknesses of the upper and lower plastic sheet components and the upper and lower FIBERGLASS sheets of the reinforcement structure is substantially uniform over the entire x-ray region of the body board to provide substantially uniform absorption of x-rays passed through the x-ray region of the body board in a direction generally normal to its flat upper support surface. Hence, despite the non-uniform thickness of the body board between the upper and lower shell components across the width of the body board, an image of substantially uniform density is produced on the x-ray film.

Thus, the present invention provides a body board having non-uniform thickness for spacing of the handholds from the ground which nonetheless produces x-ray images of substantially uniform density on x-ray film of x-rays taken through the body board.

BRIEF DESCRIPTION OF THE DRAWINGS

In the drawings, wherein like elements are referenced alike:

FIG. 3 is an end elevational view of the body board of FIG. 1, showing the handholds spaced from the ground by the runners, and a hand inserted through one of the hand holds;

FIG. 4 is a sectional view of the body board of FIG. 1 showing the reinforcement structure disposed in the hollow interior of the outer plastic shell;

Figure 1:
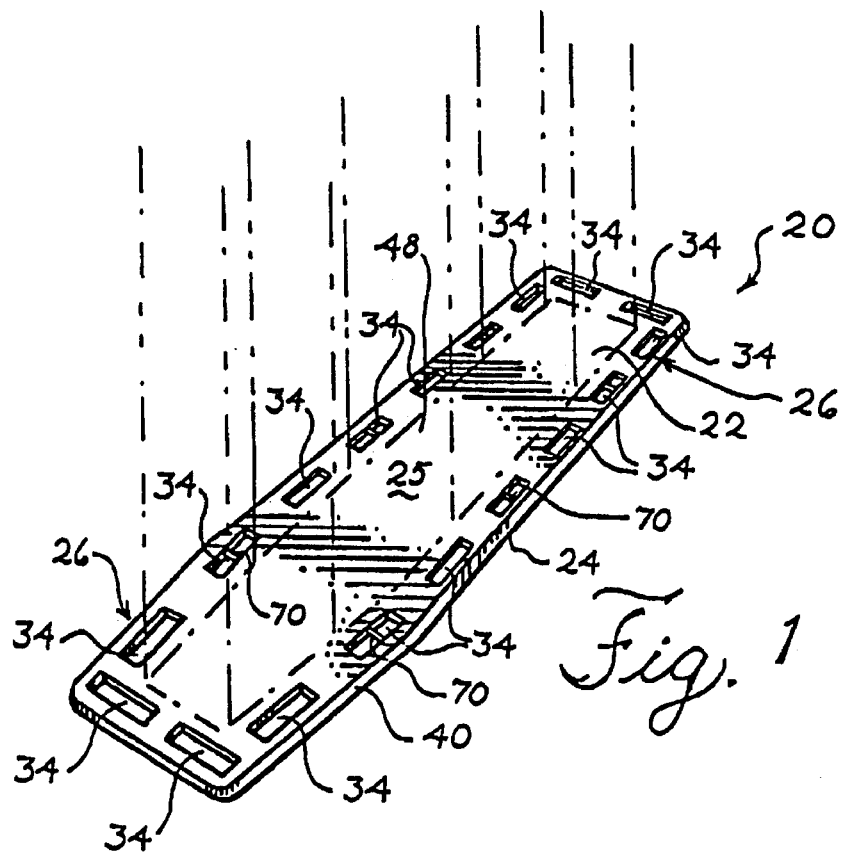
FIG. 1 is a perspective view of a body board embodying various features of the present invention.
Figure 5:
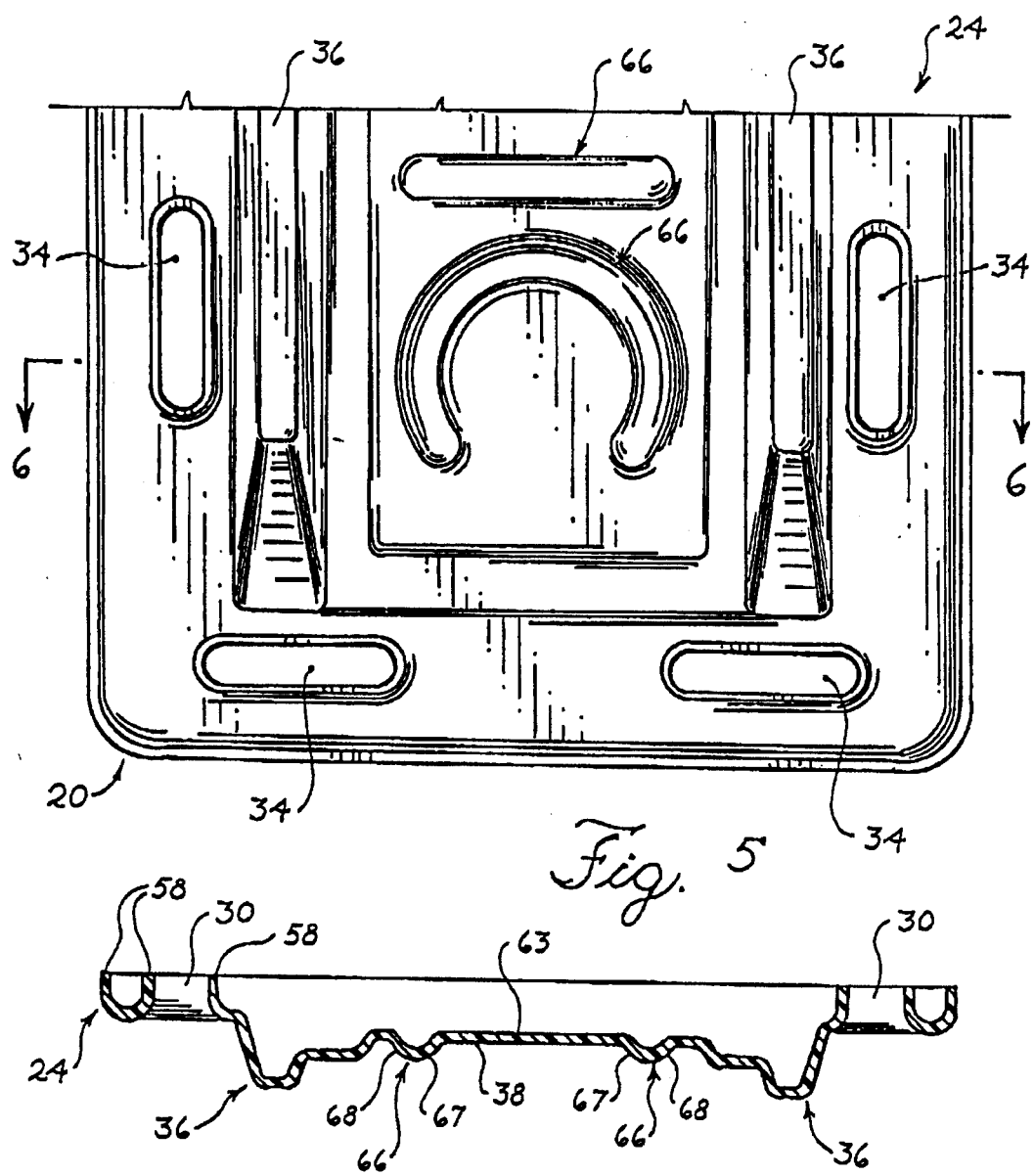
Figure 6:
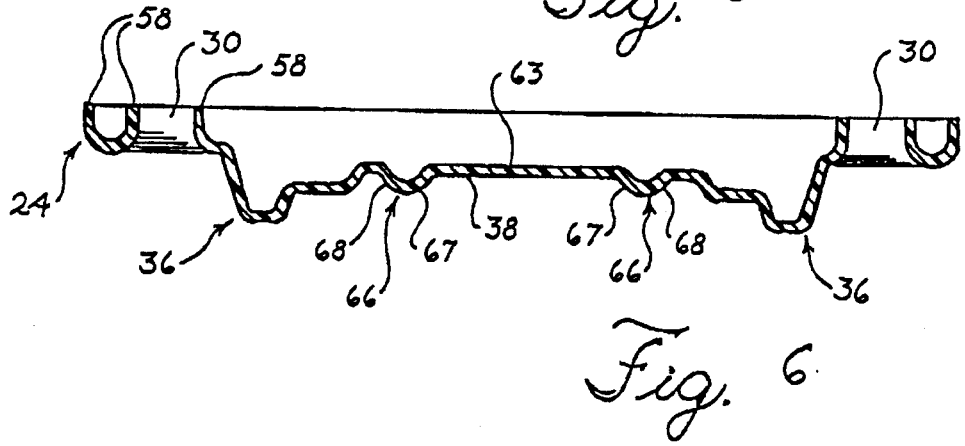

FIG. 5 is an enlarged, partial view of the lower plastic shell component of the body board of FIG. 1, showing identifying indicia formed in its underside;

FIG. 6 is a sectional view of the body board taken along line 6—6 of FIG. 5, and illustrating the contour of the indentifying indicia of FIG. 5;

FIG. 7 is a top, plan view of the body board of FIG. 1;

FIG. 8 is an end elevational view of the front end of the body board of FIG. 7;

FIG. 9 is a side elevational view of the body board of FIG. 7;

FIG. 10 is an end elevational view of the rear end of the body board of FIG. 7;

FIG. 11 is a perspective view of the body board of FIG. 7; and

FIG. 12 is a bottom view of the body board of FIG. 7.

DETAILED DESCRIPTION OF THE PREFERRED EMBODIMENTS

A body board embodying various features of the present invention is illustrated in FIGS. 1–12, and referred to generally by reference numeral 20. The body board 20 comprises an upper elongated plastic component, referred to generally by reference numeral 22, and a lower elongated plastic component, referred to generally by reference numeral 24. The upper and lower components 22 and 24 are substantially co-extensive and bonded together about their peripheries to form a shell 26. The shell 26 defines a hollow interior portion 28 between the upper component 22 and lower component 24. The shell 26 also defines a central, elongated x-ray region 25, which will be described in detail below.

The upper and lower components 22 and 24 each have a plurality of integrally formed elongated slots 30 and 32, respectively, which register with one another upon assembly of the upper and lower components 22 and 24 to define a plurality of handholds 34 disposed adjacent the periphery 40 of the shell 26. The upper and lower components 22 and 24 are bonded together about the peripheries of the handholds 34 to maintain a sealed, hollow interior between the upper and lower components 22 and 24. The handholds 34 are made sufficiently long and wide to receive the fingers of individuals carrying the body board 20.

The lower component 24 is preferably a plastic sheet of uniform thickness which is curved to define a pair of integral, generally parallel, longitudinally extending runners 36 depending downwardly from its underside 38. As best seen in FIGS. 3 and 4, the runners 36 serve to space the periphery 40 of the shell 26, at which the handholds 34 are disposed, from the ground on which the body board 20 rests. The runners 36 thus provide access for the users to insert their fingers through the handholds 34 for gripping the body board 20 at the handholds 34, without the requirement of first raising or tilting the body board 20 to gain sufficient access the handholds 34, as shown in FIG. 3.

As best seen in FIG. 4, the runners 36 are each defined by an inner side 42 and an outer side 44 and a bottom side 46. The inner and outer sides 42 and 44 of the runners 36 both extend at an angle off of vertical, to eliminate the formation of lines of high density on x-rays or other radiographs, as described further below. The bottom side 46 of the runners 36 extend substantially parallel to the flat supporting surface 48 of the upper component 22, whereby when the body board 20 is placed on a level surface such as the ground 52, as shown in FIG. 3, the bottom side 46 of the runners 36 rest upon the level ground surface 52 with the flat supporting surface 48 being substantially parallel to the level surface 52.

As discussed above, it is desirable that the body board 20 allow the taking of x-rays of an injured person while the person remains laying on the body board. Hence, the body board 20 must be translucent to x-rays or other diagnostic waves. Still further, it is important that the body board 20 not produce lines of high density on x-ray film upon passage of x-rays through the x-ray region 25 of the body board 20 in a direction generally normal to the flat supporting surface 48, as in FIG. 1.

It has been found that a shell alone, without additional internal support, does not provide sufficient structural support to prevent significant sagging of the body board under loads typically encountered with transport of persons. Making the body board of solid plastic, rather than providing only an outer shell, produces a body board which is undesirably heavy. Hence, conventional body boards are filled with polymeric foam within the plastic shell, since foam is lightweight yet still provides additional resistance to deflection of the body board.

As best seen in FIG. 4, the novel body board 20 of the present invention has significantly greater thickness between its upper and lower components 22 and 24 at the runners 36 than the region between the runners 36. Were the outer shell 26 to be filled with polymeric foam, as with conventional planar body boards, x-rays passed through the body board 20 in a direction generally normal to the supporting surface 48 would produce lines of high density on the x-ray film corresponding to the location of the runners 36. That is, with a foam filled shell 26, the foam would be thicker at the runners. Therefore, x-says would be required to pass through a greater amount of material at the runners 36 than in the region between the runners, resulting in greater x-ray absorption at the runners as compared to the region between the runners, resulting in lines of high density on the x-ray film at the runners as compared to the density of the x-ray film in the region between the runners. As stated above, it is important that the body board 20 not produce lines of high density on the x-ray film, since such lines may mask injuries of the patient or give a false indication of injuries of the patient.

In the illustrated embodiment, the x-ray region 25 of the body board 20 extends from the outer side 44 of one of the runners 36 to the outer side 44 of the other runner 36, and it is important that x-rays taken through the body board 20 over the entire x-ray region impinge upon the x-ray with substantially uniform density. Particularly with regard to injuries of the patient which may be diagnosed by subtle lines on the x-ray film, the relatively high density image produced on the x-ray film at the location corresponding to the runners, which is realized with foam filled body boards of the prior art, may mask such injuries. The body board 20 of the present invention overcomes this problem, and provides integral runners 36 for spacing the handholds 34 from the ground 52, while still providing generally uniform absorption of x-rays passed through the x-ray region of the body board, including the runners 36, despite the large thickness of the body board at the runners 36 relative to the thickness of other portions of the x-ray region 25 of the body board.

In accordance with one aspect of the present invention, substantially uniform x-ray absorption over the entire x-ray region is realized by a reinforcement structure 50 disposed within the hollow interior portion 28 of the outer shell 26, between the upper component 22 and lower component 24, as shown in FIG. 4. The reinforcement structure described in detail below provides adequate strength, has substantially uniform low cross-section density and is light weight. The illustrated reinforcement structure 50 comprises a lower reinforcement member 54 and an upper reinforcement member 56, both of which are preferably formed of FIBERGLASS material, with the outer lip 58 of the lower reinforcement member 54 bonded to the outer lip 60 of the upper reinforcement member 56.

As seen in FIG. 4, though the upper and lower fiberglass reinforcement members 54 and 56 are bent or curved several times across their widths, to provide increased resistance to longitudinal bending of the body board 20, neither the upper or lower reinforcement members 54 or 56 extend vertically over any portion. Likewise, no portion of either the upper or lower components 22 and 24 of the shell 26 extend vertically over any portion of the x-ray region 25 of the body board.

Therefore, x-rays passed through the body board 20 substantially perpendicularly to the support surface 48, at any location within the x-ray region 25, pass through the upper shell component 22, the upper reinforcement member 56, the lower reinforcement member 54, and the lower shell component 24 before impinging on x-ray film disposed beneath the body board 20.

Since the upper and lower shell components 22 and 24, and upper and lower reinforcement members 56 and 54, are each substantially uniform in thickness over the portions thereof within the x-ray region 25 of the body board, and no portion of any of these elements 22, 24, 56, and 54 which is disposed within the x-ray region 25 extends substantially vertically, x-rays passed through any portion of the x-ray region 25 of the body board pass through substantially the same amount of material. Hence, x-rays passed through the x-ray region 25 of the body board 20 are substantially uniformly absorbed by the body board over the entire x-ray region, with no significant lines of high density being produced, despite the fact that the thickness of the body board over the x-ray region 25 varies considerably.

With continued reference now to FIG. 4, x-rays passed through the x-ray region 25 of the body board 20 are represented by arrows A, B, C and D. The x-rays at A, B, C and D each pass through substantially the same amount of x-ray translucent material. This is representative of the fact that x-rays passed through any portion of the x-ray region 25 of the body board 20 pass through substantially the same amount of x-ray translucent material, so that x-rays are absorbed by the body board substantially uniformly over the entire x-ray region 25.

Specifically, the x-rays at A pass at a normal angle through each of the upper shell component 22, upper reinforcement member 56, lower reinforcement member 54, and lower shell component 24 in passing through the body board 20. Likewise, the x-rays at B pass at a normal angle through each of the upper shell component 22, upper reinforcement member 56, lower reinforcement member 54, and lower shell component 24 in passing through the body board 20, whereby the x-rays are absorbed by the body board substantially the same at both A and B despite the fact that the body board is thicker at A than at B.

The x-rays at C pass at a normal angle through the upper shell component 22, at a non-normal angle through the upper reinforcement member 56, and at a normal angle through the lower reinforcement member 54 and lower shell component 24. The x-rays at C pass through a slightly greater amount of material of the upper reinforcement member 56 than the x-rays at A and B, because the portion of the upper reinforcement member 56 at C is disposed at a non-normal angle with respect to the x-rays. However, since the portion of the upper reinforcement member 56 at C extends significantly off of vertical, the thickness which the upper reinforcement member 56 presents to the x-rays at C, as compared to the thickness which the upper reinforcement member 56 present to the x-rays at A and B, is generally insignificant. Hence, the amount of x-ray absorption by the upper reinforcement component 56 is substantially the same at C as it is at A and B.

Similarly, the x-rays at D pass at a normal angle through the upper shell component 22, and then pass at a non-normal angle through each of the upper reinforcement component 56, lower reinforcement component 54, and lower shell component 24. In accordance with the above discussion, since each of the upper reinforcement component 56, lower reinforcement component 54, and lower shell component 24 extend at an angle significantly off of vertical at D, the increased thickness which these angled portions present to the x-rays relative to the normally extending portions at A and B, is insignificant. Hence, the x-ray absorption of each of the upper reinforcement member 56, lower reinforcement member 54, and lower shell component 24 at C is substantially the same as the x-ray absorption of each of these elements at A and B.

From the foregoing, it should be apparent that x-rays passed through the body board 20, substantially normal to the supporting surface 48, will be absorbed substantially uniformly over any portion of the x-ray region 25. Accordingly, the body board 20 of the present invention lends itself to use in x-raying of patients lying on the support surface 48, without producing any lines of high density over the x-ray region 25 of the body board. Importantly, the x-ray region 25 includes the runners 36 which, although significantly thicker than the other portions of the x-ray region 25, do not produce lines of high density on the x-ray film.

Each of the x-rays A, B, C, and D, as well as x-rays passed through any other area of the x-ray region, all pass through the same amount of air in passing from the x-ray source to the x-ray film. The fact that over certain portions of the x-ray region 25 a greater amount of the air which the x-rays pass through may be disposed within the outer shell 26 of the body board rather than externally of the shell does not affect the uniformity of x-ray absorption by the air. That is, the air absorbs the same amount of x-ray energy regardless of whether the air is disposed interiorly of the shell 26 or outwardly of the shell 26. Hence, the total x-ray absorption realized between the x-ray source and the x-ray film, including the upper and lower shell components 22 and 24, the upper and lower reinforcement members 56 and 54, and the air, is substantially uniform over the entire x-ray region 25 of the body board 20.

With still further reference to FIG. 4, in the illustrated embodiment of the body board 20, the lower reinforcement member 54 is disposed directly adjacent the lower shell component 24 and conforms substantially to the contour of the lower shell component 24. The upper reinforcement member 56 is bent or curved several times over the span between its lips 60. The corrugation of the upper reinforcement member 56 provides additional structural support to resist longitudinal bending of the body board without having any portion of the upper reinforcement member 56 extending vertically. As shown in FIG. 4, the peaks 62 of the upper reinforcement member 56 abut, and preferably are bonded to, the underside 61 of the upper shell component 22. The valleys 64 of the upper reinforcement member 56 abut, and preferably are bonded to, the upper side 63 of the lower reinforcement member 54. Accordingly, the reinforcement structure 50 is sandwiched between, and bonded to, the upper and lower plastic shell components 22 and 24.

In an alternative configuration of the upper reinforcement member 56, the upper reinforcement member 56 of the embodiment of FIG. 4 is curved or arcuate to define rounded peaks 62 and valleys 64, rather than having sharp bends or creases as in the embodiment of FIG. 4.

The invention is not limited to the particular shapes depicted in the drawings. An infinite variety of different shapes may be employed for any or all of the components including the upper and lower shell components 22 and 24, and the upper and lower reinforcement members 56 and 54. An important criteria in designing a suitable body board 20 is that the amount of material of each of the components which x-rays pass through in a direction substantially normal to the upper supporting surface 48 is substantially uniform over any portion of the x-ray region 25. By forming each of the upper and lower shell components 22 and 24, and the upper and lower reinforcement members 56 and 54 of substantially uniform thickness and density across their width, with none of these components extending substantially vertically over any portion thereof, the aforementioned uniform x-ray absorption criteria are achieved in a body board having the structural integrity requisite for transport of both light and heavyweight persons.

By way of illustrative example, a reinforcement structure 50 in accordance with the present invention which was found to provide good results was produced as follows. A mold was made to form the upper reinforcement member 56. A 0.06 inch thick fiberglass part is made in the mold with 2 inch glass fibers and a high strength resin is applied of approximately 3.2 lbs. After the fiberglass has set to become firm (approximately one hour), the perimeter of the fiberglass is trimmed to the edge of the mold with a knife, and the formed upper reinforcement member 56 is removed from the mold.

A second mold is made to form the lower reinforcement component 54. A 0.08 inch thick fiberglass part is made, with 2 inch fibers and a high strength resin applied of approximately 3.8 lbs. While the resin is still wet, the upper reinforcement member 56 is placed on top of the lower reinforcement member 54. The two members 54 and 56 are then bonded together to form a reinforcement structure 50.

The reinforcement structure 50 is bonded with a high shear strength adhesive to the lower plastic shell component 24 which was vacuum formed and trimmed. Adhesive is then applied around the perimeter edge of the lower plastic shell component 24 and the flutes of the corrugated upper reinforcement member 56 and the upper plastic shell component 24 are bonded thereto. This sandwiched assembly is placed into a compression press to hold even form while the adhesive is curing. The assembly is removed from the compression press and acetone-based glue is applied around the outer edge and in the handholds at an even rate to seal and bond the upper and lower plastic shell components 22 and 24 together.

Further representative dimensions and materials for the body board 20 of the present invention are listed below. Additionally, approximations of the bending stresses and deflections realized at the center of the body board 20 constructed in accordance with the present invention, for both uniform loading distributed over the body board, and point loading at the center of the body board, are provided below. Manifestly, the dimensions and materials detailed herein are representative only, and the invention is in no way limited to the specifics delineated herein.

| ANALYSIS OF BODY BOARD | | |
|---|---|---|
| OUTER SHELL OF BOARD | | |
| LENGTH | 72.000 | INCHES |
| WIDTH | 18.000 | INCHES |
| EDGE THICK | 0.875 | INCHES |
| EDGE WIDTH | 3.000 | INCHES |
| NEAR CENTER THIC | 1.250 | INCHES |
| NEAR CTR WIDTH | 2.625 | <INCHES |
| CENTER THICK | 1.000 | INCHES |
| CENTER WIDTH | 4.500 | INCHES |
| RUNNER HEIGHT | 0.700 | INCHES |
| RUNNER WIDTH OD | 1.125 | INCHES |
| CASE GAGE | 0.125 | INCHES |
| MAX THICKNESS | 1.950 | <INCHES |
| REINFORCEMENT STRUCTURE | | |
| RUNNER HEIGHT | 1.700 | <INCHES |
| RUNNER FLANGE | 0.875 | <INCHES |
| NEAR CENTER HGT | 1.000 | <INCHES |
| NEAR CENTER FLG | 0.750 | INCHES |
| CENTER HEIGHT | 0.750 | <INCHES |
| CENTER FLANGE | 0.750 | INCHES |
| FILLER GAGE | 0.100 | INCHES |
| LOADING ON BOARD | | |
| LOAD AT CENTER | 200 | POUNDS |
| LOAD UNIFORM | 500 | POUNDS |
| MODULUS OF MATERIALS | | |
| PLASTIC SHELL | 20,000 | |
| FIBERGLASS REINFORCEMENT | 2,500,000 | |

-continued

ANALYSIS OF BODY BOARD

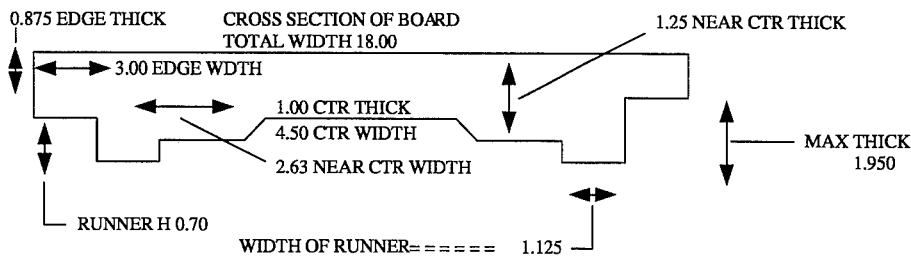

CROSS SECTION OF BOARD
0.875 EDGE THICK, TOTAL WIDTH 18.00, 1.25 NEAR CTR THICK
3.00 EDGE WDTH, 1.00 CTR THICK, 4.50 CTR WIDTH, 2.63 NEAR CTR WIDTH, MAX THICK 1.950
RUNNER H 0.70, WIDTH OF RUNNER = 1.125

| | | | | | |
|---|---|---|---|---|---|
| MOMENT OF INERTIA OF CASE | | | | H | 0.875 |
| EDGE, BOTH = | I = B*H*H*H/12 | | | B*2 | 6.000 |
| OUTSIDE SURFACES | | 0.335 | | | |
| | | | | T | 0.125 |
| INSIDE SURFACES | | 0.122 | | H–T | 0.625 |
| NET INERTIA OF EDGE | | | 0.213 | | |
| | | | | H | 1.000 |
| CENTER = | I = B*H*H*H/12 | | | B | 4.500 |
| OUTSIDE SURFACES | | 0.375 | | | |
| | | | | T | 0.125 |
| INSIDE SURFACES | | 0.158 | | H–T | 0.750 |
| NET INERTIA OF CENTER | | | 0.217 | | |
| | | | | H | 1.250 |
| NEAR CTR, BOTH = | I = B*H*H*H/12 | | | B*2 | 5.250 |
| OUTSIDE SURFACES | | 0.854 | | | |
| | | | | T | 0.125 |
| INSIDE SURFACES | | 0.438 | | H–T | 1.000 |
| NET INERTIA OF NEAR CENTER | | | 0.417 | | |
| | | | | H | 1.700 |
| RUNNER, BOTH = | I = B*H*H*H/12 | | | B*2 | 2.250 |
| OUTSIDE SURFACES | | 0.921 | | | |
| | | | | T | 0.125 |
| INSIDE SURFACES | | 0.572 | | H–T | 1.450 |
| NET INERTIA OF RUNNER | | | 0.350 | | |
| TOTAL INERTIA OF BODY | | | 1.19625 | | |
| CONVERT FIBERGLASS MODULUS TO PLASTIC = FIBERGLASS/PLASTIC MODULUS | | | | | |
| RATIO OF MODULUS = | | | 12.500 | | |
| THEN RATIO * FIBERGLASS MOMENT OF INERTIA | | | | | |
| MOMENT OF INERTIA REINFORCEMENT | | | | H | 1.700 |
| RUNNER, BOTH = | I = B*H*H*H/12 | | | B*2 | 1.750 |
| OUTSIDE SURFACES | | 0.716 | | | |
| | | | | T | 0.100 |
| INSIDE SURFACES | | 0.492 | | H–T | 1.500 |
| WEBB, BOTH = | I = B*H*H*H/12 | | | B*4 | 0.400 |
| WEBB SECTION | | 0.113 | | H–T | 1.500 |
| NET INERTIA OF RUNNER | | | 4.210 | PLASTIC | |
| | | | | H | 1.000 |
| NEAR CENT, BOTH: | I = B*H*H*H/12 | | | B*2 | 1.500 |
| OUTSIDE SURFACES | | 0.125 | | | |
| | | | | T | 0.100 |
| INSIDE SURFACES | | 0.064 | | H–T | 0.800 |
| WEBB, BOTH = | I = B*H*H*H/12 | | | B*4 | 0.400 |
| WEBB SECTION | | 0.017 | | H–T | 0.800 |
| NET INERTIA OF NEAR CTR | | | 0.976 | PLASTIC | |
| | | | | H | 0.750 |
| CENTER = | I = B*H*H*H/12 | | | B | 0.750 |
| OUTSIDE SURFACES | | 0.026 | | | |
| | | | | T | 0.100 |
| INSIDE SURFACES | | 0.010 | | H–T | 0.550 |
| WEBB, BOTH = | I = B*H*H*H/12 | | | B*2 | 0.200 |
| WEBB SECTION | | 0.003 | | H–T | 0.550 |
| NET INERTIA OF CENTER | | | 0.234 | PLASTIC | |
| TOTAL INERTIA OF FILLERS | | | 5.420 | PLASTIC | |
| TOTAL INERTIA OF REINFORCEMENT | | | 6.616 | | |

BENDING STRESS, CENTER LOAD

| | | | |
|---|---|---|---|
| LENGTH | 72.000 INCHES | PLASTIC | |
| L = SUPPORT SPAN | 52.00 INCHES | E = MODULUS | 200,000 |
| P = LOAD AT CENTER | 200 POUNDS | | |

-continued

ANALYSIS OF BODY BOARD

| REACTIONS | | 100.00 POUNDS | FIBER GLASS MODULUS | 2,500,000 |
|---|---|---|---|---|
| | M = L/2*P | C | 0.975 | |
| | | I | 6.616 | |
| STRESS = M*C/I | | | 383.15 PSI | |
| DEFLECTION = P*L*L*L/48*E*I | | | 0.443 INCHES | Deflection |
| BENDING STRESS, UNIFORM LOAD | | | | |
| LENGTH | | 72.000 INCHES | | |
| L = SUPPORT SPAN | | 52.00 INCHES | | |
| LOAD | | 500 POUNDS | | |
| W = UNIFORM LOAD | | 9.615 POUNDS PER INCH OF LENGTH | | |
| REACTIONS | | 250.00 POUNDS | | |
| MOMENT = w*I*I/8 | | | 3,250.00 | |
| STRESS = M*C/I | | | 478.93 PSI | |
| DEFLECTION = 5*w*I*I*I*I/384*E*I | | | 0.692 INCHES | Defection |

In accordance with a still further aspect of the present invention, identifying indicia 66 may be molded in the underside 38 of the lower plastic shell component 24, without significantly affecting the uniformity of density of the x-ray image produced on the x-ray film. FIGS. 5 and 6 illustrate identifying indicia 66 formed in the lower plastic shell component 24. FIG. 6, which is a sectional view taken through the identifying indicia letter "C" formed in the lower plastic shell component 24 of FIG. 5, illustrates the preferred contour of the identifying indicia 66. The lower plastic shell component 24 is preferably thermoformed by known die stamping or vacuum drawing methods to form the identifying indicia 66. The method and the die used should deflect selective portions of the lower plastic shell component 24 while maintaining the substantially uniform thickness of the lower plastic shell component 24. In this regard, it is important that the inner and outer edges 67 and 68 of the identifying indicia 66 be angled or rounded, rather than extending vertically. That is, as discussed above with regard to the reinforcement structure 50, and the inner and outer sides 42 and 44 of the runners 36, vertically extending portions in any of these elements results in increased thickness thereat, producing undesirable lines of high density on x-ray film of x-rays taken through the body board. With the inner and outer edges 67 and 68 of the identifying indicia 66 being rounded or angled, as illustrated in FIG. 6, the thickness of the material is substantially uniform over the identifying indicia 66 and the region immediately surrounding the identifying indicia, so that the identifying indicia 66 does not produce lines of high density on the x-ray film. Thereby, the name of a particular ambulance company or hospital may be molded into the underside of the body board, for rapid identification of their body board 20, without concern for it adversely affecting the uniformity of the density of x-ray images.

Figure 2:
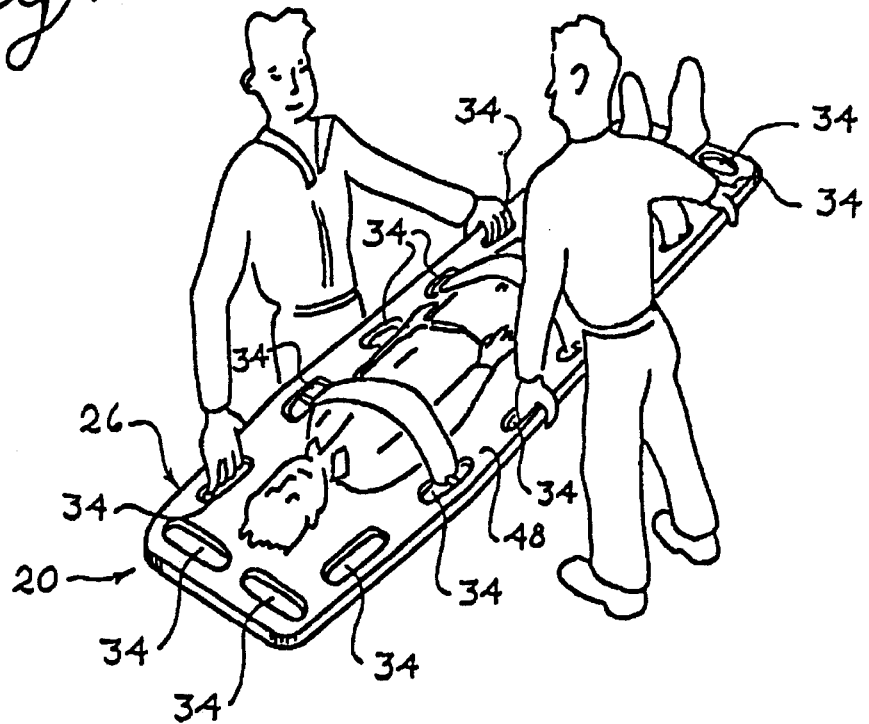
FIG. 2 is a perspective view of the body board of FIG. 1 shown with a patient strapped to the body board and being transported by two persons.

Pins 70 may be provided in one or more of the handholds 34 for engaging straps for strapping the injured person to the body board during transport, as illustrated in FIG. 2.

While the invention has been described with reference to specific, preferred embodiments, it is appreciated that changes and modification may be made to these embodiments without departing from the inventive concepts of the present invention. Hence, the invention is not limited to the specific embodiments described herein, but is intended to cover all modifications falling within the spirit and scope of the present invention as set forth in the accompanying claims.

What is claimed is:

1. A body board that is supportable on ground, comprising:

an outer plastic shell having an upper portion defining a generally flat upper surface for supporting an injured person, a lower portion defining an underside of the shell, a hollow interior between the upper and lower shell portions, and defining an x-ray region over a central portion thereof;

runners depending from the underside of the lower shell portion for supporting the body board on the ground and defining further the hollow interior; the thickness of the hollow interior at the runners and between the upper and lower portions of the outer plastic shell varying substantially across the x-ray region of the shell between the runners;

said upper and lower shell portions each being of substantially uniform thickness across the x-ray region;

reinforcement means being disposed in the hollow interior at the runners and extending through the hollow interior between the runners to cross the x-ray region of the plastic shell to provide resistance to deflection of the board under loaded conditions;

the combined thicknesses of the upper shell portion, the lower shell portion, and the reinforcement means being substantially uniform at the runners and across the x-ray region between the runners to provide substantially uniform absorption of x-rays passed through the x-ray region of the body board in a direction generally normal to its flat upper surface despite the variation in the thickness of the hollow interior at the runners and between the upper and lower portions of the outer plastic shell at the runners and across the x-ray region between the runners.

2. A body board in accordance with claim 1 in which the outer plastic shell defines a plurality of handholds adjacent its periphery, and the lower shell portion is extended downwardly over selective portions to define the runners for supporting the body board on the ground with the handholds in spaced relation from the ground.

3. A body board, comprising:

an outer plastic shell having an upper portion defining a generally flat upper surface for supporting an injured person, a lower portion defining an underside of the shell, a hollow interior between the Upper and lower shell portions, and defining an x-ray region over a central portion thereof;

the thickness of the shell between its upper portion and its lower portion varying substantially across the x-ray region of the shell;

said upper and lower shell portions each being of substantially uniform thickness across the x-ray region;

reinforcement means disposed in the hollow interior region of the plastic shell to provide resistance to deflection of the board under loaded conditions, the reinforcement means extending across the x-ray region;

the combined thicknesses of the upper shell portion, the lower shell portion, and the reinforcement means being substantially uniform across the x-ray region to provide substantially uniform absorption of x-rays passed through the x-ray region of the body board in a direction generally normal to its flat upper surface despite the variation in the thickness of the shell across the x-ray region;

the reinforcement means having a reinforcement structure extending across the x-ray region; and the reinforcement structure having a plurality of longitudinally extending bends with the entire portion of the reinforcement structure disposed within the x-ray region extending significantly off of vertical.

4. A body board, comprising:

an outer plastic shell having an upper portion defining a generally flat upper surface for supporting an injured person, a lower portion defining an underside of the shell, a hollow interior between the upper and lower shell portions, and defining an x-ray region over a central portion thereof;

the thickness of the shell between its upper portion and its lower portion varying substantially across the x-ray region of the shell;

said upper and lower shell portions each being of substantially uniform thickness across the x-ray region;

reinforcement means disposed in the hollow interior region of the plastic shell to provide resistance to deflection of the board under loaded conditions, the reinforcement means extending across the x-ray region;

the combined thicknesses of the upper shell portion, the lower shell portion, and the reinforcement means being substantially uniform across the x-ray region to provide substantially uniform absorption of x-rays passed through the x-ray region of the body board in a direction generally normal to its flat upper surface despite the variation in the thickness of the shell across the x-ray region and having a reinforcement structure;

the reinforcement means being a reinforcement structure; and the reinforcement structure comprising, an upper reinforcement member disposed within the hollow interior of the shell and extending across the x-ray region, a lower reinforcement member disposed within the hollow interior of the shell and extending across the x-ray region, said upper and lower reinforcement members each being of substantially uniform thickness across the x-ray region, said upper and lower reinforcement members each having a plurality of bends across the x-ray region to provide increased structural resistance to deflection of the body board, and the upper and lower reinforcement members extending significantly off of vertical over the portions thereof disposed within the x-ray region.

5. A body board in accordance with claim 4 in which:

the lower reinforcement member is bonded to and resides adjacent the lower shell portion and substantially conforms to the contour of the lower shell portion; and the upper reinforcement member is corrugated to define longitudinally extending ridges and grooves which are respectively bonded to the upper shell component and the lower reinforcement member.

6. A body board for resting on a ground, comprising:

a body defining a generally flat upper surface for supporting an injured person and defining an underside;

the body defining a plurality of handholds disposed adjacent its periphery;

runner means depending from the underside of the body to support the handholds adjacent the periphery of the body in spaced relation from the ground on which the body board rests to provide easy access to the handholds for insertion of fingers therethrough while the body board is resting on the ground;

the body comprising an upper, longitudinally extending plastic shell component defining the generally flat upper surface for supporting an injured person and a lower, longitudinally extending plastic shell having the underside, the upper plastic shell being bonded to the lower plastic shell to form a plastic shell and the body defining a central x-ray region spanning the pair of runners;

the thickness of the plastic shell between the upper and lower plastic shell components is substantially greater over the portions at the runners than over the portions between the runners;

a reinforcement structure is disposed within the hollow interior region of the plastic shell to provide structural resistance to bending of the spineboard under load;

said reinforcement structure comprises an upper fiberglass sheet and a lower fiberglass sheet both extending across the x-ray region and being bent several times to provide increased resistance to bending of the body board;

the upper plastic shell component and the lower plastic shell component each having substantially uniform thickness over the portions thereof disposed within the x-ray region of the body board;

the upper and lower fiberglass sheets each having substantially uniform thickness over the portions thereof disposed within the x-ray region, and extending significantly off of vertical over the portions thereof disposed within the x-ray region; and the combined thicknesses of the upper and lower plastic shell components, and the upper and lower fiberglass reinforcement sheets are substantially uniform across the x-ray region to provide substantially uniform absorption of x-rays passed through the body board in a direction generally normal to its flat upper surface despite the relatively large thickness of the body board at the runners.

7. A body board in accordance with claim 6 in which the lower plastic shell component is deflected over predetermined portions to form identifying indicia, with the thickness of the lower plastic shell being maintained substantially constant over the x-ray region including the location of the identifying indicia, and the edges of the identifying indicia extending at an angle off of vertical, with substantially uniform absorption of x-rays over the x-ray region including the identifying indicia so that the identifying indicia do not form lines of high density on x-ray film.

8. A body board, comprising:

an upper, longitudinally extending plastic shell component defining a generally flat upper surface for supporting an injured person;

a lower, longitudinally extending plastic shell component being bonded to the upper component to form a shell which defines a hollow interior;

the shell defining a plurality of handholds about its periphery and defining an x-ray region over a central, longitudinally extending portion thereof, said x-ray region encompassing the hollow interior located centrally of the plurality of handholds;

the lower plastic shell component defining runners for spacing the handholds from the ground to allow insertion of fingers through the handholds while the body board rests on the ground;

the hollow interior being defined further by the runners and the x-ray region encompassing the runners;

the thickness of the hollow interior between the upper component and the lower component of the shell being significantly greater at the runners than in the region between the runners;

said upper and lower components each being of substantially uniform thickness across the x-ray region;

reinforcement means disposed in the hollow interior region of the plastic shell to provide resistance to deflection of the board under loaded conditions, the reinforcement means being located at the runners in the hollow interior and extending across the x-ray region between the runners; and the combined thicknesses of the upper component, the lower component, and the reinforcement means being substantially uniform at the runners and across the x-ray region to provide substantially uniform absorption of x-rays passed through the body board in a direction generally normal to its flat upper surface despite the relatively large thickness of the body board at the runners.

\* \* \* \* \*